United States Patent [19]

Mauldin

[11] Patent Number: 5,945,459
[45] Date of Patent: Aug. 31, 1999

[54] PREPARATION OF HIGH ACTIVITY CATALYSTS; THE CATALYSTS AND THEIR USE

[75] Inventor: Charles H. Mauldin, Baton Rouge, La.

[73] Assignee: Exxon Research and Engineering Co, Florham Park, N.J.

[21] Appl. No.: 09/187,883

[22] Filed: Nov. 6, 1998

Related U.S. Application Data

[62] Division of application No. 08/847,958, Apr. 22, 1997, Pat. No. 5,863,856.

[51] Int. Cl.$^6$ .................................................. C07C 27/00
[52] U.S. Cl. ............................................ 518/715; 518/700
[58] Field of Search ..................................... 518/715, 700

[56] References Cited

U.S. PATENT DOCUMENTS

| | | | |
|---|---|---|---|
| 4,234,462 | 11/1980 | Bondar et al. | 252/463 |
| 4,409,131 | 10/1983 | Fetchin | 502/263 |
| 4,568,450 | 2/1986 | Ting et al. | 208/216 |
| 4,977,126 | 12/1990 | Mauldin | 502/242 |

Primary Examiner—Paul J. Killos
Assistant Examiner—Jafar Parsa
Attorney, Agent, or Firm—Jay Simon

[57] ABSTRACT

A process for the preparation of a catalyst useful for conducting carbon monoxide hydrogenation reactions, especially a Fischer-Tropsch catalyst, use of the catalyst for conducting such reactions, especially Fischer-Tropsch reactions, and the composition produced by said process. In the preparation of the catalyst, a solution of a multifunctional carboxylic acid having from about 3 to 6 total carbon atoms, preferably about 4 to 5 total carbon atoms, is employed to impregnate and disperse a compound or salt of rhenium and a compound or salt of a catalytic metal, or metals, e.g., copper or an Iron Group metal such as iron, cobalt, or nickel onto a refractory inorganic oxide support, e.g., titania. The rhenium, which need be present only in small amount permits full and complete reduction of the catalytic metal, or metals, dispersed by the acid. Higher catalyst activities with lower rhenium loadings are thus achieved than in previous preparations where higher concentrations of rhenium were required to both effectively disperse, and reduce the catalytic metal, or metals, during the preparation. Surprisingly, as little as about $\frac{1}{10}$ of the rhenium is required to accomplish the reduction promotion where the dispersion is effected with the acid.

11 Claims, No Drawings

5,945,459

PREPARATION OF HIGH ACTIVITY CATALYSTS; THE CATALYSTS AND THEIR USE

This is a division, of application Ser. No. 847,958, filed Apr. 22, 1997, now U.S. Pat. No. 5,863,856.

1. FIELD OF THE INVENTION

This invention relates to a process, or method, for the production of a high activity catalyst by dispersion of rhenium and a catalytic metal, or metals, particularly copper or an Iron Group metal, notably cobalt, onto a refractory inorganic oxide support, notably titania; the catalyst; its reduction, and use of the catalyst for conducting carbon monoxide hydro-genation reactions, especially Fischer-Tropsch reactions.

2. BACKGROUND

Carbon monoxide hydrogenation reactions are well known. For example, Fischer-Tropsch synthesis processes, or processes for the catalytic conversion of synthesis gas, i.e., a mixture of hydrogen and carbon monoxide, to high quality distill ate fuels or mixtures of $C_5+$ liquid hydrocarbons are well known. For example, the Group VIII non-noble metals, iron, cobalt, and nickel have been widely used to catalyze Fischer-Tropsch reactions, and these metals have been deposited on various supports, and promoted with various other metals. In U.S. Pat. No. 4,568,663, e.g., there is disclosed a process of this type which utilizes a highly active catalyst composition constituted of cobalt-rhenium-titania, $Co—Re—Ti\ O_2$. This catalyst is made, e.g., by impregnating a concentrated aqueous solution of cobalt nitrate and perrhenic acid onto a titania support by the conventional incipient wetness method, drying, and then calcining to decompose the nitrate salt to the oxide. Several important functions are served by the rhenium. A major function is served by rhenium during the calcination of the catalyst, during which cobalt nitrate decomposes to cobalt oxide, in that it causes the cobalt oxide to become more highly dispersed. It also preserves the cobalt oxide in highly dispersed state under high temperature oxidizing conditions, such as is found useful for regenerating cobalt catalysts. It is also a function of the rhenium to lower the temperature of the reduction of cobalt oxide to the zero valence state, which is required to achieve full activity. Rhenium makes it easier to more fully reduce the cobalt. High dispersal, and full reduction of the cobalt results in a more active catalyst. This result however does not come without cost, for rhenium is a relatively expensive commodity. Thus, there exists a need for means to better disperse the cobalt with a lesser amount of rhenium, find means for recovering the rhenium, or find other more available, less expensive materials for promoting the dispersion, and reduction of the metals.

In U.S. Pat. No. 1,914,557 there is disclosed the use of carboxylic acids, e.g., malic acid, as complexing agents in the preparation of supported metal catalysts. A solution of a "metallic-organo complex" is evaporated onto a support as an adherent sticky mass, or coating, forming a catalyst the coating of which does not readily flake or dust off. In U.S. Pat. No. 4,409,131 there is disclosed the preparation of supported catalysts containing cobalt or nickel and molybdenum made by impregnation of the support with stable solutions of cobalt or nickel complexed with carboxylic acid, e.g., citric acid, compatible with ammonium molybdate. U.S. Pat. No. 4,568,449 discloses a process for preparing catalysts wherein a support is premoistened in a first step with a carboxylic acid, and second step wherein the support is impregnated with a solution containing molybdenum, nickel and phosphorus. In accordance with U.S. Pat. No. 4,568,450 codeposition of metals and carboxylic acid is made from a single solution in forming the supported catalyst.

3. SUMMARY OF THE INVENTION

The present invention, which meets this and other needs, relates to a novel process for the preparation of a catalyst useful for the hydro-genation of carbon monoxide, especially a Fischer-Tropsch catalyst, the catalyst, and process for the use of this catalyst for conducting such reactions, especially Fischer-Tropsch synthesis reactions, i.e., reactions for the production of $C_5+$ liquid hydrocarbons from hydrogen and carbon monoxide. In the preparation of the catalyst, a preformed particulate refractory inorganic solids support, preferably titania, is impregnated with (a) a compound, or salt, of a catalytic metal, or metals, suitably copper or an Iron Group metal, (b) a compound, or salt, of rhenium, and (c) a multi-functional carboxylic acid. In impregnating the support, the support is contacted, preferably, with a single solution containing all of (a), (b), and (c). The multi-functional carboxylic acid is sufficient to distribute the compound or salt of the catalytic metal, copper or Iron Group metal in highly dispersed form, onto the support; and, the rhenium is sufficient to produce full reduction of the dispersed metal. Whereas rhenium has been used in the past to produce both of these functions, a far lesser amount of rhenium is required to produce both dispersion and reduction of the metal when the rhenium is used in conjunction with the acid.

The multi-functional carboxylic acid is characterized as having the formula

$$HOOC—(CRR^1)_n—COOH$$

wherein n is an integer defining the length of the chain of carbon atoms between the two terminal carboxylic acid groups and is equal to or greater than 1 and can range as high as about 4, and preferably n ranges from about 2 to about 3; and substituents R and $R^1$ are the same or different, and are selected from the group consisting of hydrogen, hydrocarbyl, i.e., hydrocarbon groups per se, or hydrocarbon groups which contain oxygen, nitrogen, or the like, suitably alkyl, e.g., methyl, ethyl, propyl, etc., hydroxyl, carboxyl, amino, alkoxy and the like. Malonic acid, aspartic acid, tartaric acid, succinic acid, citric acid, glutaric acid, glutamic acid, adipic acid, and the like are exemplary of these multi-functional carboxylic acids.

It has been found that the copper or Iron Group metal can be more effectively dispersed onto the support via use of the multi-functional carboxylic acid than with rhenium, as a consequence of which no rhenium is required to effect a full, and complete dispersion of the catalytic metal, or metals. However, some rhenium is required since its presence enables a more complete and full reduction of the dispersed copper or Iron Group metal to the zero valent state. Accordingly, in the practice of this invention, a small amount of a compound or salt of rhenium, and both a compound or salt of copper or an Iron Group metal and a multi-functional carboxylic acid, are employed to disperse the copper or Iron Group metal, and rhenium, onto the solids support component of the catalyst during the impregnation; dispersion of the copper or Iron Group metal into the preformed catalyst resulting from the presence of multi-functional carboxylic acid, while the rhenium is effective in permitting full reduction of the catalyst after calcination. The copper or Iron Group metal compound, and rhenium compound, are thus effectively dispersed during the impregnation step, and during calcination the multi-functional carboxylic acid is removed by combustion leaving behind crystallites of well dispersed oxides of the copper or Iron Group metal and the rhenium. Essentially complete reduction of the crystallites of the metals is achieved on contact of the calcined catalyst with a reducing agent, e.g., hydrogen. Surprisingly, in the preparation of a catalyst it is found that considerably less rhenium is required overall when prepared with a multi-functional carboxylic acid to produce a full, similar level of activity in a reduced copper or Iron Group metal/rhenium catalyst of given composition, used in a carbon monoxide hydrogenation or Fischer-Tropsch reaction, than with a reduced catalyst of corresponding composition, used in a similar carbon monoxide hydrogenation or Fischer-Tropsch reaction at similar process conditions, made in a preparation otherwise similar except that the catalyst was made without use of a multi-functional carboxylic acid.

4. DETAILED DESCRIPTION

The catalysts are formed by deposition of the catalytic metal, or metals, on a previously pilled, pelleted, beaded, extruded, spray dried, or sieved support material by the impregnation method. In preparing the catalysts, the metals are deposited from solution on the support in preselected amounts to provide the desired absolute amounts, and weight ratios of the metals being deposited. Catalysts constituted of cobalt and rhenium supported on titania, or a titania-containing support, with or without the addition of an additional metal, or metals, promoter or modifier, e.g., ruthenium, hafnium, zirconium, titanium, chromium, thoria, copper, etc., exhibit superior hydrocarbon synthesis characteristics and provide high selectivities in the conversion of synthesis gas to $C_5+$ hydrocarbon liquids. Suitably, the metals are deposited by contact and treatment of the support with a solution, suitably an aqueous solution, which contains the multi-functional carboxylic acid, e.g., glutamic acid, in addition to the compound or salt of the copper or Iron Group metal, e.g., cobalt, or the compound or salt of the rhenium, or both the compound or salt of the copper or Iron Group metal and the compound or salt of the rhenium.

The catalytic metal, copper or Iron Group metal, and the rhenium can be deposited from solution in sequence, or codeposited from the same impregnating solution, and the multi-functional carboxylic acid can be deposited from solution in sequence with the copper or Iron Group metal, and rhenium, or codeposited with the copper or Iron Group metal and the rhenium. The multi-functional carboxylic acid can thus be codeposited with a catalytic metal, or metals, or it can be deposited from solution by a separate impregnation. Preferably however, the multi-functional carboxylic acid is codeposited with the copper or Iron Group metal and the rhenium. The volume of impregnating solution used in an impregnation usually ranges from about 1 to about 20 times the volume of the support, and is generally carried out at ambient or elevated temperature. Preferably, the impregnation is carried out at conditions of incipient wetness, and at essentially ambient temperature. In accordance with the incipient wetness technique, as is known, the volume of the impregnating solution and amount of metals is predetermined to correspond to the maximum volume which will just fill the internal pore volume of the support, with no liquid in excess on impregnation of the support. Various refractory inorganic oxide supports are useful in the formation of catalysts pursuant to the practice of this invention. Exemplary of such supports are titania, which is preferred, silica, silica-alumina, alumina, and the like.

Highly concentrated metal salt solutions are most desirable for preparing hydrocarbon synthesis catalysts because they generate the highest metal loading per impregnation, higher metal loadings leading in turn to higher catalytic activity. Common salts or compounds of the catalytic metals can generally be used. However, it has been found that the nitrate salt, especially in the case of cobalt is preferred because it is the most readily available and least expensive salt and, more importantly, it possesses the highest degree of solubility in water. Cobalt acetate is also suitable, although it is less water soluble. Cobalt chloride and sulfate are not suitable for making hydrocarbon synthesis catalysts, presumably because of poisoning by residual anions not removed in the calcination, regardless of the promotion of dispersion by multi-functional carboxylic acids. Solvents other than water may be used, like alcohols, ketones and the like, but are generally not preferred because of lower metal salt solubility and added manufacturing cost. Suitable rhenium compounds are the common water soluble ones, especially perrhenic acid and ammonium perrhenate.

The catalytic metal, copper or Iron Group metal, preferably cobalt, is added to the support in amount sufficient to provide from about 2 percent to about 50 percent, preferably from about 5 percent to about 35 percent of the elemental metal, based on the total weight of the finished catalyst (dry basis). The maximum metal loading that can be obtained per impregnation will depend upon the support pore volume, which will in turn depend upon the support composition, and the metal concentration in the impregnating solution. Multiple impregnation/calcination steps may be used to obtain high final metal loadings. Other metals, e.g., thorium, cerium, hafnium, uranium and the like can be added if desired to modify or promote the activity of the finished catalyst. These metals when present are added in weight ratio to copper or Iron Group metal ranging above about 0.01:1, preferably from about 0.025:1 to about 0.1:1. Rhenium is added to the support in concentration sufficient to provide a weight ratio of elemental rhenium:elemental copper or Iron Group metal (e.g., Re/Co weight ratio) in the finished catalyst ranging from about 0.005:1 to about 0.2:1, preferably from about 0.01:1 to about 0.1:1 (dry basis). The multi-functional carboxylic acid is added to the support in concentration sufficient to disperse the copper or Iron Group metal compound throughout the support, from about 2 percent to about 30 percent, preferably from about 6 percent to about 25 percent, of the multi-functional carboxylic acid generally being adequate to fully accomplish this objective; and it does this even more effectively than the rhenium. Preferably, the multi-functional carboxylic acid is added to metal salt impregnating solution such that the mole ratio of the carboxylic acid compound to metal is about 0.1:1 to about 0.6:1, preferably from about 0.2:1 to about 0.5:1. The catalyst, after impregnation, is dried by heating, suitably at temperatures ranging from about 30° C. to about 120° C., in an air, nitrogen or other gas stream or under vacuum. The metals are converted to an oxide form by calcination, suitably at temperature ranging from about 200° C. to about 550° C., preferably from about 250° C. to about 400° C., and the multi-functional carboxylic acid is burned, combusted, and removed from the catalyst. The catalyst is then activated by reduction, suitably by contact with hydrogen at temperature ranging from about 250° C. to about 550° C., preferably from about 275° C. to about 425° C., for periods ranging from about 0.5 hour to about 24 hours at pressures ranging from above ambient to about 40 atmospheres.

The catalyst produced in accordance with this invention, particularly those comprised of the Iron Group metals, corresponds in composition to those known, and useful in the conversion of synthesis gas to waxy, paraffinic $C_5+$ hydrocarbons. The Fischer-Tropsch, F-T, or hydro-carbon synthesis process is carried out at temperatures of about 160° C. to about 325° C., preferably from about 190° C. to about 260° C., pressures of about 5 atm to about 100 atm, preferably about 10–40 atm and gas hourly space velocities of from about 300 V/Hr/V to about 20,000 V/Hr/V, preferably from about 500 V/Hr/V to about 15,000 V/Hr/V. The stoichiometric ratio of hydrogen to carbon monoxide in the synthesis gas is about 2.1:1 for the production of higher hydrocarbons. However, $H_2$/CO ratios of 1:1 to about 4:1, preferably about 1.5:1 to about 2.5:1, more preferably about 1.8:1 to about 2.2:1 can be employed. These reaction conditions are well known and a particular set of reaction conditions can be readily determined by those skilled in the art. The reaction may be carried out in virtually any type reactor, e.g., fixed bed, moving bed, fluidized bed, slurry, bubbling bed, etc. The waxy, or paraffinic product from the F-T reactor, or reactor utilizing the catalyst made pursuant to the practice of this invention is an essentially non-sulfur, non-nitrogen, non-aromatics containing hydrocarbon. It is a liquid product which can be produced and shipped from a remote area to a refinery site for further chemically reacting and upgrading to a variety of products, or produced and upgraded at a refinery site. Separator products taken from the F-T reactor, i.e., hot separator and cold separator liquids, respectively, i.e., $C_4$–$C_{15}$ hydrocarbons, constitute high quality paraffin solvents which, if desired, can be hydrotreated to remove olefin impurities, or employed without hydrotreating to produce a wide variety of non-toxic wax products. The reactor wax, or $C_{16}+$ liquid hydrocarbons from the F-T reactor, on the other hand, can be upgraded by various hydro-conversion reactions, e.g., hydrocracking, hydroisomerization catalytic dewaxing, isodewaxing, etc., or combinations thereof, to produce such products as stable, environmentally benign, non-toxic mid-distillates, diesel and jet fuels, e.g., low freeze point jet fuel, high cetane jet fuel etc., isoparaffinic solvents, lubricants, e.g., lube oil blending components and lube oil base stocks suitable for transportation vehicles, non-toxic drilling oils suitable for use in drilling muds, technical and medicinal grade white oils, chemical raw materials and various specialty products.

The following non-limiting examples, and comparative demonstrations, exemplify the more salient and preferred embodiments of the invention.

EXAMPLES

A series of catalysts were prepared by impregnating a support, generally a rutile or anatase titania support, but including alumina and silica, with a concentrated aqueous solution of cobalt nitrate and perrhenic acid via the incipient wetness technique. In most of the preparations, as tabulated hereafter, different multi-functional carboxylic acids were dissolved in cobalt nitrate/perrhenic acid solutions, the multi-functional carboxylic acid generally being added in concentration of 0.306 mole per mole of elemental cobalt. The amount of water present in each impregnating solution was adjusted for the weight of the acid added to maintain a constant 15 wt. % cobalt, calculated as elemental cobalt, in the solution. In a base case preparation, for comparative purposes, no multi-functional carboxylic acid was added to the cobalt nitrate/perrhenic acid solution. In some cases the catalysts were made by single impregnations (about 7 wt. % Co in the finished catalysts) in the exploration of preparation variables. In other cases, a second impregnation was applied to increase metals loadings and produce finished catalysts more typical of those which may be employed in large scale operations. In each preparation, after impregnation the catalyst was dried and then calcined in air to decompose the nitrate salt to the oxide and burn off the organic additive.

Most of the preps were made with a spray-dried titania support. Two batches were used which were obtained by calcining the raw spray-dried support at two different temperatures, as indicated in the following table. An extruded alumina support ground to 63–125 micron size and a spray-dried silica support were also used in a few examples.

| Designation | Calcination Temp. ° C. | Surface Area $m^2/g$ | $H_2O$ Pore Volume, cc/g |
|---|---|---|---|
| Rutile[1] | 1000 | 19 | 0.33 |
| Anatase[2] | 500 | 29 | 0.50 |
| Alumina | 540 | 189 | 0.48 |
| Silica | 800 | 170 | 1.02 |

[1] 94% Rutile - 6% Anatase $TiO_2$
[2] 27% Rutile - 73% Anatase $TiO_2$

Each of the catalysts were characterized by the following tests.

$O_2$ Chemisorption: measured with $O_2$ pulses in helium at 25° C. after reduction in hydrogen at 450° C. Results are expressed as micromoles $O_2$ per gram and as an O/Co atomic ratio. The oxygen chemi-sorption is a measure of the relative dispersion of cobalt oxide on the support.

Fixed Bed Hydrocarbon Synthesis (HCS) Test: conducted at 200° C., 280 psig, with a syn gas feed of 65$H_2$—31CO—4Ne and GHSV adjusted as required to give conversion around 70% at 16–20 hours on stream. Catalysts were diluted with 1–7 parts by volume of titania to minimize temperature gradients in a 0.25 inch ID reactor, used to conduct the test. Prior to introducing the syn gas, the catalyst is reduced in situ in hydrogen for one hour at the temperature shown in the Tables. Conversion of CO and selectivity to methane (mole % of CO converted to $CH_4$) are shown in the Tables. Values for "Cobalt Productivity," which has the units of liters of CO converted per hour per gram of cobalt, are also included in each of the Tables.

Table 1: Effect of Multi-Functional Carboxylic Acid Composition

Table 1 summarizes the results obtained with different multi-functional carboxylic acids as impregnation aids for dispersing the cobalt throughout a support. The examples were made with the rutile titania support, without any rhenium promoter. The key results are given in the last column, i.e., reference being made to the O/Co chemisorption data. The catalysts are grouped according to the length of the longest carbon chain in the organic acid. Example 1 demonstrates for comparative purposes a run made without use of any multi-functional carboxylic acid in the preparation. Examples 2–7 show minimal improvement when the catalysts are produced by dispersion of the cobalt with 3C multi-functional carboxylic acids. In Examples 8–14, on the other hand, wherein 4C to 6C multi-functional carboxylic acids were used in the preparations, higher relative dispersions were obtained. These acids give an O/Co over 0.4 compared to a value of less than 0.3 for the base case. From a list of the structures of the acids tested, the critical structural features of the preferred acids are shown to have a total carbon chain of at least four atoms, preferably 5 atoms. The multi-functional carboxylic acids, it is believed, improve cobalt dispersion by covering the titania surface with a thin "blanket" of the acid, which provides a trap for molten anhydrous cobalt nitrate as it is generated in the pores during the drying/calcination process. In the absence of something so polar to bind to, the colbalt salt probably coalesces into larger crystallites as it decomposes to the oxide. The preference for the longer chain length is especially significant; noting, e.g., how relatively ineffective a shorter chain is, like malonic acid. This longer chain, it is believed, does not chelate to a single species, but rather attaches itself to two entities, the cobalt on one end and the titania on the other. There appears no evidence of complexation between either glutamic or citric acid and the Co+2 in the starting solution by UV spectroscopy, though complexation may occur later as the mixture is heated and dried in the calcination process. This is fortunate because preformed complexes appear to be much less soluble, and hence would perform poorly in the very concentrated solutions as used herein.

The Cobalt Productivity values for Examples 1–14, it will be observed, fail to show a significant activity credit despite the improved cobalt dispersion. The problem lies in achieving full reduction of the improved dispersion; a problem solved by including a small amount of rhenium as reduction promotor as subsequently illustrated.

Comparison of Example 15 with Examples 16 and 17 illustrates that the dispersion advantage seen for the two best multi-functional carboxylic acids, glutamic acid and citric acid, is also present after a second impregnation is applied to achieve higher cobalt loading. As will be observed, the reducibility problem however is dampened somewhat by the higher metal loading (it is easier to reduce 12% Co than 7% Co), so an activity credit is observed to augment the dispersion credit. Example 16 represents a very active Re-free Co-TiO$_2$ catalyst.

Table 2: Effect of Multi-Functional Carboxylic Acid Loading

The molar ratio of the multi-functional carboxylic acid to elemental cobalt was varied with glutamic acid, citric acid, and tartaric acid, as shown by Examples 18–29, summarized in Table 2. It is clear from these data that an optimum ratio exists between about 0.2 and about 0.5, with the best dispersion credit occurring at about 0.3 mole of acid per mole of cobalt for all three acids. Preference for this ratio may reflect more the ratio of the acid to the support surface area rather than to the cobalt (these ratios are proportional to each other in most of these preps). For example, the larger concentrations of acid may be less effective because the "blanket" is getting too thick, supra. The optimum acid:Co ratio may thus be a function of the support surface area.

Table 3: Effect of Rhenium

The incorporation of some rhenium permits maximization of the hydrocarbon synthesis activity of the catalyst. The acids function extremely well in generating cobalt dispersion, but the activity of the catalyst does not correspondingly increase unless the reducibility of the dispersed cobalt oxide to the active zero-valent state is improved. Simply applying higher temperature in the reduction step does not solve the problem because the growth of a titania overlayer with titania, or sintering of the cobalt metal in the case of alumina or silica, are processes that are favored by higher temperature and counteract any positive gains in reduction. The addition of some rhenium however greatly improved the extent of cobalt oxide reducibility at 300–450° C. Examples 30–34 of Table 3, base case examples not of this invention, show that activity gradually increases with Re:Co ratios up to about 0.09, but there is no further improvement in activity at higher Re:Co ratios. Examples 35–39, on the other hand wherein glutamic acid is used to promote dispersion on the base case rutile support, show a rapid increase in activity as rhenium is introduced into these glutamic preps. Cobalt Productivity over 5, which is higher than the best of the base case catalysts, is achieved with only a 0.01 Re:Co ratio. Examples 40–45 show similar findings with the higher pore volume, anatase form of the support. Here activity also increases dramatically with rhenium, with an optimum ratio occurring at about 0.04, which is half the base case optimum.

While Cobalt Productivity is very useful in assessing cobalt effectiveness in the hydrocarbon conversion reaction, Weight Productivity is the activity measure that best defines the relative performance of a catalyst in a slurry reactor. Weight Productivity results (cc CO converted per hour per gram of catalyst) for Examples 30–45 show that the higher metal loading obtained with the higher pore volume, anatase support adds significantly to the advantage gained with the glutamic-low rhenium recipe to generate higher activity catalysts. Comparison of the catalyst of Example 45, with half the base case Re:Co ratio, is twice as active as the catalyst of base case Example 34.

Table 4: Other Metals and Supports

Table 4 provides Examples 46–49 showing that dispersion improvement with glutamic acid occurs with other Group VIII metals besides cobalt, e.g., copper and nickel. Examples 50–54 show that glutamic and citric acids improve cobalt dispersion on alumina, with or without added rhenium. Examples 55–56 show that glutamic acid improves cobalt dispersion on a silica support. Solutions as concentrated as possible at room temperature were used in these preps. In the Examples using organic acids, the mole ratio of the organic acid to cobalt in the impregnating solution was 0.3.

TABLE 1

Effect of Multi-Functional Carboxylic Acid Compositions

| Example | Multi-Functional Carboxylic Acid (Acid/Co = 0.306) | Wt. % Co | H$_2$ Temp | Density | GHSV | CO Conv | Mol % CH$_4$ | Co Prod | Chemis | O/Co |
|---|---|---|---|---|---|---|---|---|---|---|
| | Single Impregnations: | | | | | | | | | |
| 1 | none | 7.06 | 450 | 1.13 | 875 | 70 | 5.1 | 2.46 | 165 | 0.276 |
| 2 | glycine | 6.99 | 450 | 1.08 | 750 | 68 | 5.0 | 2.16 | 222 | 0.375 |
| 3 | alanine | 6.81 | 450 | 1.08 | 850 | 67 | 5.2 | 2.48 | 184 | 0.319 |
| 4 | leucine | 7.06 | 450 | 1.08 | 875 | 76 | 4.3 | 2.79 | 211 | 0.353 |
| 5 | serine | 6.85 | 450 | 1.08 | 900 | 70 | 5.0 | 2.73 | 224 | 0.386 |
| 6 | threonine | 7.23 | 450 | 1.08 | 900 | 77 | 4.5 | 2.84 | 241 | 0.393 |

TABLE 1-continued

Effect of Multi-Functional Carboxylic Acid Compositions

| Example | Multi-Functional Carboxylic Acid (Acid/Co = 0.306) | Wt. % Co | $H_2$ Temp | Density | GHSV | CO Conv | Mol % $CH_4$ | Co Prod | Chemis | O/Co |
|---|---|---|---|---|---|---|---|---|---|---|
| 7 | malonic acid | 7.15 | 450 | 1.08 | 625 | 71 | 4.6 | 1.84 | 182 | 0.300 |
| 8 | tartaric acid | 6.75 | 450 | 1.08 | 800 | 67 | 5.0 | 2.35 | 268 | 0.469 |
| 9 | aspartic acid | 7.00 | 450 | 1.08 | 850 | 68 | 5.1 | 2.45 | 253 | 0.426 |
| 10 | succinic acid | 5.53 | 450 | 1.08 | 750 | 72 | 5.0 | 2.89 | 218 | 0.465 |
| 11 | citric acid | 7.10 | 450 | 1.08 | 850 | 71 | 5.1 | 2.52 | 336 | 0.558 |
| 12 | glutamic acid | 7.39 | 450 | 1.08 | 1150 | 74 | 4.2 | 3.41 | 345 | 0.551 |
| 13 | glutaric acid | 7.15 | | | | | | | 268 | 0.442 |
| 14 | adipic acid | 5.41 | 450 | 1.08 | 650 | 71 | 5.7 | 2.53 | 204 | 0.455 |
| | Double Impregnations: | | | | | | | | | |
| 15 | none | 12.65 | 450 | 1.37 | 1400 | 72 | 4.6 | 1.86 | 239 | 0.223 |
| 16 | glutamic acid | 12.07 | 450 | 1.37 | 2800 | 64 | 5.3 | 3.47 | 475 | 0.464 |
| 17 | citric acid | 12.87 | 450 | 3.37 | 2200 | 70 | 4.8 | 2.79 | 411 | 0.377 |

TABLE 2

Effect of Multi-Functional Carboxylic Acid Loading

| Example | Acid/Co mol ratio | Wt. % Co | $H_2$ Temp | Density | GHSV | CO Conv | Mol % $CH_4$ | Co Prod | Chemis | O/Co |
|---|---|---|---|---|---|---|---|---|---|---|
| | Glutamic Acid | | | | | | | | | |
| 18 | 0.102 | 6.71 | 450 | 1.08 | 750 | 67 | 5.0 | 2.22 | 173 | 0.304 |
| 19 | 0.204 | 7.14 | 450 | 1.08 | 875 | 70 | 5.1 | 2.54 | 262 | 0.433 |
| 20 | 0.306 | 7.39 | 450 | 1.08 | 1150 | 74 | 4.2 | 3.41 | 345 | 0.551 |
| | Citric Acid | | | | | | | | | |
| 21 | 0.102 | 7.08 | | | | | | | 121 | 0.202 |
| 22 | 0.204 | 7.20 | | | | | | | 182 | 0.298 |
| 23 | 0.306 | 7.10 | 450 | 1.08 | 850 | 71 | 5.1 | 2.52 | 336 | 0.558 |
| 24 | 0.502 | 6.58 | | | | | | | 271 | 0.486 |
| 25 | 1.15 | 6.71 | | | | | | | 191 | 0.336 |
| | Tartaric Acid | | | | | | | | | |
| 26 | 0.191 | 7.42 | | | | | | | 219 | 0.348 |
| 27 | 0.306 | 6.75 | 450 | 1.08 | 800 | 67 | 5 | 2.35 | 268 | 0.469 |
| 28 | 0.408 | 7.52 | | | | | | | 244 | 0.383 |
| 29 | 0.549 | 6.3 | | | | | | | 185 | 0.347 |

TABLE 3

Effect of Rhenium

| Example | Wt. % Co | Wt % Re | Re/Co | $H_2$ Temp | Density | GHSV | Co Conv | Mol % $CH_4$ | Chemis | O/Co | Co Prod |
|---|---|---|---|---|---|---|---|---|---|---|---|
| | Base Case On Rutile Support Without Multi-functional Carboxylic Acid | | | | | | | | | | |
| 30 | 11.72 | 0 | 0 | 375 | 1.43 | 1750 | 73 | 5 | 243 | 0.245 | 2.44 |
| 31 | 12.12 | 0.139 | 0.0115 | 375 | 1.43 | 2000 | 70 | 5.1 | 336 | 0.327 | 2.59 |
| 32 | 11.79 | 0.252 | 0.0214 | 375 | 1.43 | 2500 | 73 | 5.5 | 360 | 0.360 | 3.46 |
| 33 | 11.79 | 0.697 | 0.0591 | 375 | 1.43 | 3000 | 73 | 5.7 | 394 | 0.394 | 4.16 |
| 34 | 11.32 | 1.07 | 0.0945 | 375 | 1.43 | 3500 | 73 | 5.9 | 395 | 0.412 | 5.05 |
| | Glutamic Acid Used With Rutile Support | | | | | | | | | | |
| 35 | 12.07 | 0 | 0 | 450 | 1.37 | 2800 | 64 | 5.8 | 475 | 0.464 | 3.47 |
| 36 | 12.84 | 0.049 | 0.0039 | 450 | 1.37 | 3500 | 73 | 4.7 | 545 | 0.501 | 4.65 |
| 37 | 11.16 | 0.108 | 0.0097 | 450 | 1.37 | 3600 | 73 | 5.1 | 562 | 0.594 | 5.50 |
| 38 | 12.59 | 0.509 | 0.0404 | 450 | 1.37 | 4000 | 70 | 5.5 | 636 | 0.596 | 5.19 |
| 39 | 12.22 | 1.093 | 0.0894 | 450 | 1.37 | 4000 | 71 | 5.5 | 683 | 0.660 | 5.43 |
| | Glutamic Acid Used With Anatase Support | | | | | | | | | | |
| 40 | 16.92 | 0 | 0 | 450 | 1.23 | 1400 | 73 | 4.6 | 415 | 0.289 | 1.57 |
| 41 | 16.08 | 0.061 | 0.0038 | 450 | 1.23 | 2200 | 72 | 5 | 516 | 0.379 | 2.56 |

TABLE 3-continued

Effect of Rhenium

| Example | Wt. % Co | Wt % Re | Re/Co | H$_2$ Temp | Density | GHSV | Co Conv | Mol % CH$_4$ | Chemis | O/Co | Co Prod |
|---|---|---|---|---|---|---|---|---|---|---|---|
| 42 | 17.27 | 0.128 | 0.0074 | 375 | 1.23 | 3800 | 68 | 4.5 | 588 | 0.402 | 3.89 |
| 43 | 16.72 | 0.327 | 0.0196 | 375 | 1.23 | 5500 | 67 | 5.1 | 702 | 0.495 | 5.73 |
| 44 | 16.52 | 0.649 | 0.0393 | 375 | 1.23 | 5500 | 69 | 4.8 | 691 | 0.494 | 5.98 |
| 45 | 16.44 | 1.472 | 0.0895 | 375 | 1.23 | 5600 | 70 | 5.7 | 900 | 0.646 | 6.20 |

TABLE 4

Other Metals and Supports

| Example | Support | Multi-Functional Carboxylic Acid | Wt % Co | Wt % Cu | Wt % Ni | Wt % Re | Chemis |
|---|---|---|---|---|---|---|---|
| 46 | TiO$_2$(Rutile) | none | 0 | 8.4 | 0 | 0 | 14 |
| 47 | TiO$_2$(Rutile) | glutamic acid | 0 | 8.8 | 0 | 0 | 86 |
| 48 | TiO$_2$(Anatase) | none | 0 | 0 | 10 | 0 | 167 |
| 49 | TiO$_2$(Anatase) | glutamic acid | 0 | 0 | 10 | 0 | 223 |
| 50 | Al$_2$O$_3$ | none | 16.6 | 0 | 0 | 0 | 329 |
| 51 | Al$_2$O$_3$ | glutamic acid | 16.6 | 0 | 0 | 0 | 653 |
| 52 | Al$_2$O$_3$ | citric acid | 16.6 | 0 | 0 | 0 | 599 |
| 53 | Al$_2$O$_3$ | none | 16.6 | 0 | 0 | 1.4 | 1002 |
| 54 | Al$_2$O$_3$ | glutamic acid | 16.6 | 0 | 0 | 1.4 | 1570 |
| 55 | SiO$_2$ | none | 17.4 | 0 | 0 | 0.77 | 776 |
| 56 | SiO$_2$ | glutamic acid | 18.1 | 0 | 0 | 0.80 | 1576 |

Additional runs were made with malic acid, a 4C chain dicarboxylic acid with a hydroxyl group on the second carbon; one wherein a titania support was contacted and impregnated with a solution of malic acid and cobalt nitrate and a second by forming a cobalt metal complex with cobalt nitrate in water and sodium hydroxide, and heating as described by Example 13 of U.S. Pat. No. 1,914,557.

First, a catalyst was prepared by the incipient wetness technique as in the foregoing; a solution containing cobalt nitrate and malic acid, in a mole ratio of acid:Co=0.3, being impregnated from aqueous solution into a rutile titania support as described by Examples 1–14, with the following results:

| Example | Multi-Functional Carboxylic Acid | Wt. % Co. | Chemis | O/Co |
|---|---|---|---|---|
| 57 | Malic acid | 7.06 | 297 | 0.496 |

As indicated by the chemisorption data, malic acid behaves in this procedure much like other 4C acids, i.e., like tartaric and succinic. Thus, used in this procedure there is a consistent relationship between the acid structure, notably carbon chain length, and the promotion of cobalt dispersion.

Quite different from the impregnation, or incipient wetness procedure, the Patentee makes a solution of the metal complex and then evaporates this solution onto a support. Using Example 13 of the patent as a guide, a catalyst was made according to the following:

11.55 grams of cobalt nitrate [Co(NO$_3$)$_2$—6H$_2$O] was dissolved in 100 ml H$_2$O. 3.29 grams of NaOH was dissolved in 50 ml H$_2$O and added slowly to the stirred cobalt nitrate solution. The resulting precipitate of cobalt hydroxide was filtered through a Buchner funnel and washed with 50 ml of H$_2$O. All of the wet precipitate (9.9 grams) was added to a solution of 5.5 grams malic acid in 75 ml H$_2$O.

A dark violet solution formed after sonicating for about 10 minutes at 50° C. Some light pink solid remained undissolved. The solution containing the cobalt malate complex was decanted into a flask containing 30.0 grams of the rutile titania support. The solution was then evaporated onto the support with a rotary evaporator. The impregnated catalyst was calcined in the quartz reactor tube with an air flow of 375 cc/min at 300° C. for 3 hours. The finished catalyst was found to contain 5.47 wt% Co, which is lower than the 7% target because of the incomplete dissolution of the cobalt hydroxide in the presence of the malic acid. Oxygen chemisorption was 93 micromoles 02/gram, which corresponds to an O:Co ratio of 0.201.

This prep was thus found to be significantly inferior to those made according to the incipient wetness procedure, stipra. Cobalt dispersion as measured by the relative oxygen chemisorption is especially poor, only 0.201 O/Co versus 0.496 in the preceding example. Thus, there is a disadvantage in forming the cobalt-acid complex as opposed to a simple mixture of the nitrate salt and the acid. Furthermore, there is the disadvantage of lower solubility of the complex compared to the nitrate salt and acid mixture. As indicated by this test, it is not possible to obtain a 15 wt% Co concentration in the impregnating solutions, as is done in the method of this invention. Even as little as 3 wt% Co would not dissolve. Lower cobalt solubility means less cobalt loading per impregnation, which will translate to a significant debit in the catalyst manufacturing cost, if viable at all.

Spectroscopic evidence suggests that complex formation between the cobalt and the di-acid does not occur at all in an impregnating solution as practiced in accordance with the present invention; even if some kind of complex formed in-situ, during the drying of the impregnated catalyst. In accordance with the practice of this invention, some type of binding with the support surface area may occur thereby providing a very polar "blanket" which favors a better dispersion of the cobalt nitrate salt, right before it decomposes. This theory rationalizes the preference for the five-carbon acids: the best dispersion promoters being those acids which are long enough to disfavor bonding both ends to the cobalt but rather favor bonding to cobalt with one end and to the support with the other.

Complete reduction of the catalytic metal, or metals, is required to achieve full catalyst activity. Full catalyst activity however can be achieved by only a small amount of rhenium, even at lower reduction temperatures. Surprisingly, as little as 1/10 of the base case amount of rhenium will satisfactorily promote the reduction when the dispersion is accomplished by the presence of the acid. Activity with this small amount of rhenium is generally about 20% higher than in the base, whereas it is about 20% lower without the rhenium. It therefore becomes possible with the copresence of the acid to make drastic reductions in the amount of rhenium employed while yet achieving full dispersion and reduction of the catalyst.

What is claimed is:

1. A process for the production of $C_5+$ liquid hydrocarbons from a hydrogen and carbon monoxide synthesis gas comprising contacting the synthesis gas with a catalyst at reaction conditions, the catalyst formed by the steps comprised of: impregnating a refractory inorganic oxide support with a solution containing (a) a compound or salt of a catalytic metal or metals, (b) a multi-functional carboxylic acid having the formula $$HOOC-(CRR^1)-COOH$$

where n is an integer from 1 to 4, R and $R^1$ are the same or different, and are selected from the group consisting of hydrogen, hydrocarbyl, hydroxyl, carboxyl, amino and alkoxy, and sufficient to disperse the compound or the salt onto the support, (c) a compound or salt of rhenium, and drying, and removing the multifunctional carboxylic acid, and forming oxides of the metals on the support.

2. The process of claim 1 wherein the catalytic metal or metals comprise cobalt.

3. The process of claim 1 wherein at least a portion of the $C_5+$ liquid hydrocarbons is upgraded by subjecting such portion to fractionation or conversion.

4. The process of claim 3 wherein the conversion comprises non-catalytic processing.

5. The process of claim 3 wherein the conversion comprises catalytic processing.

6. The process of claim 5 wherein the catalytic processing comprises hydroconversion.

7. The process of claim 6 wherein the hydroconversion comprises hydroisomerization.

8. The process of claim 7 wherein the hydroisomerization produces diesel fuel.

9. The process of claim 7 wherein the hydroisomerization produces jet fuel.

10. The process of claim 6 wherein the hydroconversion comprises catalytic dewaxing.

11. The process of claim 10 wherein the catalytic dewaxing produces lube oil blending components and lube oil base stocks.

* * * * *